United States Patent
Zou et al.

(10) Patent No.: US 11,039,810 B2
(45) Date of Patent: Jun. 22, 2021

(54) THREE-DIMENSIONAL ULTRASONIC IMAGING METHOD AND SYSTEM

(71) Applicant: Shenzhen Mindray Bio-Medical Electronics Co., Ltd., Shenzhen (CN)

(72) Inventors: Yaoxian Zou, Shenzhen (CN); Muqing Lin, Shenzhen (CN); Zhijie Chen, Shenzhen (CN); Yi Xiong, Shenzhen (CN); Bin Yao, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 281 days.

(21) Appl. No.: 16/255,033

(22) Filed: Jan. 23, 2019

(65) Prior Publication Data
US 2019/0159754 A1    May 30, 2019

Related U.S. Application Data

(63) Continuation of application No. 15/048,832, filed on Feb. 19, 2016, now Pat. No. 10,213,183, which is a
(Continued)

(30) Foreign Application Priority Data

Aug. 21, 2013    (CN) .......................... 201310367753.1

(51) Int. Cl.
*A61B 8/00*    (2006.01)
*A61B 8/08*    (2006.01)
(Continued)

(52) U.S. Cl.
CPC .............. *A61B 8/0866* (2013.01); *A61B 8/14* (2013.01); *A61B 8/461* (2013.01); *A61B 8/483* (2013.01);
(Continued)

(58) Field of Classification Search
CPC ......... A61B 8/0866; A61B 8/14; A61B 8/461; A61B 8/5207; A61B 8/523; A61B 8/483;
(Continued)

(56) References Cited

U.S. PATENT DOCUMENTS 5,588,435 A    12/1996 Weng
10,433,819 B2 *  10/2019 Lee ...................... A61B 8/0866
(Continued)

FOREIGN PATENT DOCUMENTS

CN    101011266 A    8/2007
CN    101238987 A    8/2008
(Continued)

OTHER PUBLICATIONS

Pilu et al., Three Dimensional Ultrasound Examination of the Fetal Central Nervous Systems, 2007, pp. 233-245, vol. 30, Published by John Wiley & Sons, Ltd.
(Continued)

*Primary Examiner* — Joel Lamprecht
(74) *Attorney, Agent, or Firm* — Kory D. Christensen (57) ABSTRACT

A three-dimensional ultrasonic imaging method includes transmitting an ultrasonic wave to a fetal head; receiving an ultrasonic echo, obtaining an ultrasonic echo signal, and obtaining the three-dimensional volume data of the fetal head according to the ultrasonic echo signal; according to the characteristics of a median sagittal section of the fetal head, detecting the median sagittal section in the three-dimensional volume data; and displaying the median sagittal section.

9 Claims, 6 Drawing Sheets

Related U.S. Application Data continuation of application No. PCT/CN2014/071441, filed on Jan. 25, 2014.

(51) Int. Cl.
  *G06T 7/68* (2017.01)
  *A61B 8/14* (2006.01)

(52) U.S. Cl.
  CPC ............ *A61B 8/523* (2013.01); *A61B 8/5207* (2013.01); *G06T 7/68* (2017.01); *A61B 8/0808* (2013.01); *A61B 8/469* (2013.01); *A61B 8/5223* (2013.01); *G06T 2207/10136* (2013.01); *G06T 2207/30044* (2013.01)

(58) Field of Classification Search
  CPC ..... A61B 8/0808; A61B 8/5223; A61B 8/469; G06T 7/68; G06T 2207/10136; G06T 2207/30044
  See application file for complete search history.

(56) References Cited

U.S. PATENT DOCUMENTS

| | | |
|---|---|---|
| 2008/0188748 A1 | 8/2008 | Sonek et al. |
| 2010/0217123 A1 | 8/2010 | Aharon et al. |
| 2011/0054324 A1 | 3/2011 | Lee |
| 2011/0224546 A1 | 9/2011 | Lee et al. |
| 2013/0072797 A1 | 3/2013 | Lee |
| 2013/0116561 A1 | 5/2013 | Rothberg |
| 2014/0371591 A1 | 12/2014 | Jung et al. |

FOREIGN PATENT DOCUMENTS

| | | |
|---|---|---|
| CN | 101238987 A | 8/2008 |
| CN | 102754125 A | 10/2012 |
| WO | WO2013095032 A1 | 6/2013 |

OTHER PUBLICATIONS

Wei et al., "Three-dimensional ultrasound in the diagnosis of fetal agenesis of corpus callosum," Chin J Med Imaging Technol, China Academic Journal Publishing House, 2011, vol. 27, No. 8, pp. 1663-1667.

"Sonographic examination of the fetal central nervous system: guidelines for performing the 'basic examination' and the 'fetal neurosonogram'", Ultrasound in Obstetrics and Gynecology, vol. 29, No. 1, Jan. 1, 2007 (Jan. 1, 2007), pp. 109-116, XP055040876, ISSN: 0960-7692, DOI: 10.1002/uog.3909.

Kwang Hee Lee et al: "Robust Mid-Sagittal Plane Extraction in 3-D Ultrasound Fetal Volume For First Trimester Screening", Nov. 5, 2012, Computer Vision ACCV 2012, Springer Berlin Heidelberg, Berlin, Heidelberg, pp. 316-329, ISBN: 978-3-642-37443-2, XP047027130.

\* cited by examiner

THREE-DIMENSIONAL ULTRASONIC IMAGING METHOD AND SYSTEM

CROSS-REFERENCE TO RELATED APPLICATIONS

This application is a continuation of U.S. patent application Ser. No. 15/048,832, filed on Feb. 19, 2016, for THREE-DIMENSIONAL ULTRASONIC IMAGING METHOD AND SYSTEM, which claims the benefit of Chinese Patent Application No. 201310367753.1, filed on Aug. 21, 2013, both of which are incorporated herein by reference.

TECHNICAL FIELD

The present disclosure relates to medical ultrasound imaging and in particular to methods and systems for three-dimensional ultrasound imaging.

BACKGROUND

Ultrasound imaging apparatus are generally used by doctor to inspect tissues inside human body. The doctor can place an ultrasound probe onto the surface of the skin corresponding to a tissue to obtain ultrasound images of the tissue. Due to its characteristics of safety, convenience, non-invasion and low cost, etc, the ultrasound imaging has become a main assisting means for diagnosis.

Obstetrics is one of the fields where the ultrasound imaging is widely applied. With the use of the ultrasound imaging device, the affects to mother and fetus by the X rays can be avoided. Therefore, the ultrasound imaging device has better application value than other imaging device. By the ultrasound imaging device, not only the morphology of the fetus can be observed and measured, but also various information regarding the physiology or pathology of the fetus, such as the respiration or urination of the fetus, can be obtained to evaluate the health and growth states of the fetus.

When inspecting the nervous system of the fetus, the corpus callosum and the cauda cerebella are very important objects. The corpus callosum is the biggest connection fiber between the cerebral hemispheres and is responsible for the communication between the cerebral hemispheres. Deficiency or hypogenesis of the corpus callosum will lead to several complications, such as epilepsy, feeblemindedness or dyskinesia, etc. Deficiency or hypogenesis of the cauda cerebella is the symptom of Dandy-Walker syndrome. 50% of patients with the Dandy-Walker syndrome have mental retardation and feeblemindedness, and are usually accompanied by chromosome abnormalities and other deformities, with poor prognosis and high mortality rate.

Accordingly, the abnormalities of the corpus callosum and the cauda cerebella are represents of critical diseases. If they were not found during the prenatal examination, they would bring huge mental and economic burden to the family of the patient and the society. Besides, for the hospital where the examination is carried out, they may lead to medical tangles. However, the corpus callosum and the cauda cerebella are very easy to be misdiagnosed or missed during the inspection of the nervous system of the fetus. The reason is that it is very difficult to obtain the median sagittal section image of the fetus, which is the best image for observing the corpus callosum and the cauda cerebella, by a conventional two-dimensional ultrasound imaging due to the affects of the factors such as fetal position, amniotic fluid, obstruction of the nasal bone and skill of the doctors, etc. Even if the image of the median sagittal section was obtained, it would take a long time. Accordingly, many doctors have to indirectly inspect the corpus callosum and the cauda cerebella by images of other sections (such as, the cerebellum section or the thalamus section, etc.), therefore the misdiagnosis and the missed diagnosis are easy to occur.

Recently, with the widespread use of the three-dimensional ultrasound imaging, some doctors perform a three-dimensional scanning on the fetus starting from the biparietal diameter section, find out the image of the median sagittal section of the fetus by geometric transforms of obtained 3D ultrasound image data, such as manual rotation and translation, etc, and then inspect the corpus callosum and the cauda cerebella through this median sagittal section image. Although the median sagittal section image obtained by this way may have relatively lower quality than a conventional two-dimensional image, the corpus callosum and the cauda cerebella can be relatively clearly displayed, and the abnormalities of the corpus callosum and the cauda cerebella can be determined quickly and exactly. However, in order to be able to find out the median sagittal section in three-dimensional space by manual rotation and translation, the doctors must understand the three dimensional space very well. But, most doctors have no science and engineering background and lack of understanding to a three dimensional space. Therefore it is very difficult for them to manually find out the median sagittal section image from a volume data. Although it has been developed for many years, only few doctors have this skills.

SUMMARY

One of the objects of the present disclosure is to provide three dimensional ultrasound imaging methods in which the head of a fetus can be three-dimensionally imaged and the median sagittal section image of the head of the fetus can be automatically acquired.

In some embodiments, a three dimensional ultrasound imaging method is provided. The method may include: transmitting ultrasound waves towards a head of a fetus; receiving ultrasound echoes to obtain ultrasound echo signals; obtaining a three dimensional volume data of the head of the fetus based on the ultrasound echo signals; acquiring a median sagittal section image of the head of the fetus from the three dimensional volume data based on characteristics of median sagittal section image of a fetal head; and displaying the median sagittal section image.

In an embodiment, the median sagittal section image may be acquired from the three dimensional volume data based on gray characteristic of median sagittal section image of featal head.

In an embodiment, the step of acquiring a median sagittal section image of the head of the fetus from the three dimensional volume data may include: extracting sagittal section characteristic regions from the three dimensional volume data, wherein the sagittal section characteristic regions represent plane regions which have larger gray values than areas located outside both sides of the plane regions; selecting at least three characteristic points from the sagittal section characteristic regions; and determining a plane on which the median sagittal section image is located based on the at least three characteristic points.

In an embodiment, the step of acquiring a median sagittal section image of the head of the fetus from the three dimensional volume data may include: extracting at least two section images from the three dimensional volume data; extracting brain midlines from the at least two section images to obtain at least two brain midlines, wherein the brain midlines have larger gray values than areas located outside both sides of the brain midlines; and determining a plane on which the median sagittal section image is located based on a plane determined by the at least two brain midlines.

In an embodiment, the step of extracting brain midlines from the at least two section images may include: for each section image of the at least two section images, performing following steps: extracting brain midline characteristic regions from the section image, wherein the brain midline characteristic regions represent lines having larger gray values than areas located outside both sides of the lines; selecting at least two characteristic points from the brain midline characteristic regions; and determining the brain line based on the at least two characteristic points.

In an embodiment, the step of acquiring a median sagittal section image of the head of the fetus from the three dimensional volume data may also include: selecting a group of candidate section images from the three dimensional volume data; calculating a symmetry indicator for each candidate section image of the group of candidate section images to obtain a group of symmetry indicators; and selecting a characteristic symmetry indicator which satisfies a characteristic condition from the group of symmetry indicators, wherein the candidate section image corresponding to the characteristic symmetry indicator is the median sagittal section image.

In an embodiment, the group of candidate section images may be a group of longitudinal section images of the three dimensional volume data.

In an embodiment, the step of calculating a symmetry indicator for each candidate section image of the group of candidate section images may include: for each candidate section image of the group of candidate section images, performing following steps: selecting at least one pair of first region and second region outside both sides of the candidate section image, wherein the first region and the second region are symmetrical with respect to the candidate section image; and calculating the symmetry indicator of the candidate section image using data in the first region and data in the second region.

In an embodiment, the symmetry indicator may be: a sum of absolute values of differences between gray values of points being symmetrical with respect to the candidate section image in the first region and in the second region, wherein the characteristic condition is that the symmetry indicator is the smallest; and/or a correlation coefficient between the first region and the second region, wherein the characteristic condition is that the symmetry indicator is the largest; and/or an Euclidean distance between the first region and the second region, wherein the characteristic condition is that the symmetry indicator is the smallest; and/or a cosine similarity between the first region and the second region, wherein the characteristic condition is that the symmetry indicator is the largest.

In an embodiments, the step of acquiring a median sagittal section image of the head of the fetus from the three dimensional volume data may also include: obtaining a template image of median sagittal section image of a fetal head generated based on median sagittal section images of fetus which have been obtained previously; selecting a group of candidate section images from the three dimensional volume data; calculating a similarity indicator for each candidate section image of the group of candidate section images with the template image to obtain a group of similarity indicators; and selecting a characteristic similarity indicator which satisfies a characteristic condition from the group of similarity indicators, wherein the candidate section image corresponding to the characteristic similarity indicator is the median sagittal section image.

In an embodiment, the group of candidate section images may be a group of longitudinal section images of the three dimensional volume data.

In an embodiment, the method may, before selecting a group of candidate section images from the three dimensional volume data, further include aligning the three dimensional volume data and the template image to a same scale space.

In an embodiment, the step of aligning the three dimensional volume data and the template image to a same scale space may include: detecting special structural features in section images of the three dimensional volume data; and converting the three dimensional volume data into a same scale with the template image based on sizes of the special structural features.

In an embodiment, the similarity indicator may be: a sum of absolute values of differences between gray values of corresponding points in the candidate section image and in the template image, wherein the characteristic condition is that the similarity indicator is the smallest; and/or a correlation coefficient between the candidate section image and the template image, wherein the characteristic condition is that the similarity indicator is the largest; and/or an Euclidean distance between the candidate section image and the template image, wherein the characteristic condition is that the similarity indicator is the smallest; and/or a cosine similarity between the candidate section image and the template image, wherein the characteristic condition is that the similarity indicator is the largest.

In some embodiments, a three dimensional ultrasound imaging system may be provided. The system may include: a probe which transmits ultrasound waves towards a head of a fetus and receives ultrasound echoes to obtain ultrasound echo signals; a three dimensional imaging unit which obtains a three dimensional volume data of the head of the fetus based on the ultrasound echo signals and acquires a median sagittal section image of the head of the fetus from the three dimensional volume data based on characteristics of median sagittal section image of a fetal head; and a display which displays the median sagittal section image.

In the ultrasound imaging methods according to the present disclosure, the fetus may be scanned by ultrasound waves and the three dimensional volume data of the head of the fetus may be obtained. The median sagittal section image of the head of the fetus may be automatically obtained and displayed. The problem that it is difficult for the doctors to precisely position the median sagittal section image may be solved. Therefore, the doctor can conveniently observe the median sagittal section image of the head of the fetus and a large amount of important information may be presented to the doctor.

DETAILED DESCRIPTION

Figure 1:
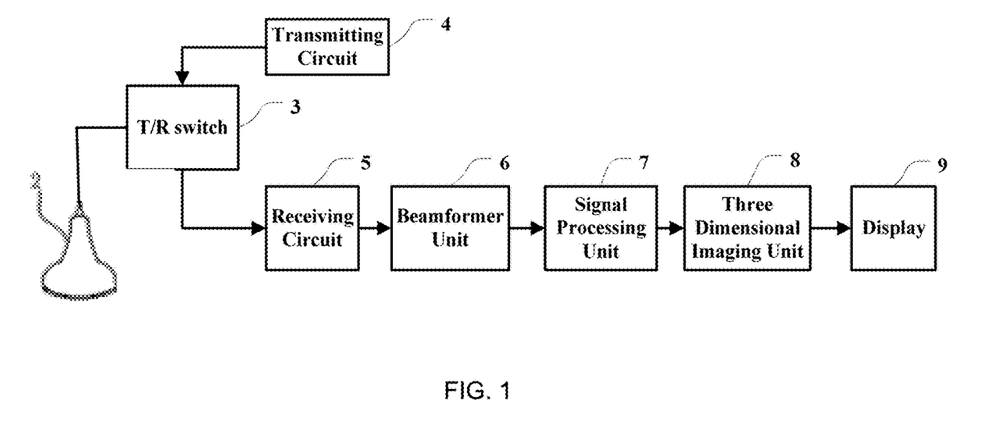
FIG. 1 is a schematic block diagram of a three dimensional ultrasound imaging system according to an embodiment of the present disclosure.

FIG. 1 schematically shows the block diagram of a three dimensional ultrasound imaging system, which may include a probe 2, a transmitting/receiving switch 3, a transmitting circuit 4, a receiving circuit 5, a beamformer unit 6, a signal processing unit 7, a three dimensional imaging unit 8 and a display 9. The transmitting circuit 4 may transmit a series of pulses which are focused by delay to the probe 2. The probe 2 may transmit ultrasound waves towards a tissue to be inspected (not shown), receive echoes (which contain information of the tissue) reflected by the tissue after a period of time and transform the echoes into electric signals (hereinafter, "ultrasound echo signals"). The receiving circuit 5 may receive the ultrasound echo signals and send them to the beamformer unit 6. The beamformer unit 6 may perform delay focusing, weighting and channel summing on the ultrasound echo signals. Then, after processed by the signal processing unit 7, the ultrasound echo signals may be sent to the three dimensional imaging unit 8, where the ultrasound echo signals may be processed to obtain three dimensional images. The three dimensional images may be displayed on the display 9.

After one cycle of the scanning of the probe 2, a three dimensional volume data in polar coordinates may be formed in the three dimensional imaging unit 8 using the ultrasound echo signals processed by the signal processing unit 7. The three dimensional volume data in polar coordinates may be converted into volume data in Cartesian coordinates through a reconstruction process to obtain a three dimensional volume data in Cartesian coordinates. The three dimensional imaging unit 8 may process the three dimensional volume data in Cartesian coordinates to obtain three dimensional images, which may be displayed on display device.

In embodiments of the present disclosure, the three dimensional imaging unit 8 of the three dimensional imaging system may further include a subunit for automatically obtaining a median sagittal section image of a fetus. The subunit can automatically obtain a median sagittal section image of the head of a fetus using the obtained three dimensional volume data of the head of the fetus (which will be described in details below).

Figure 2:
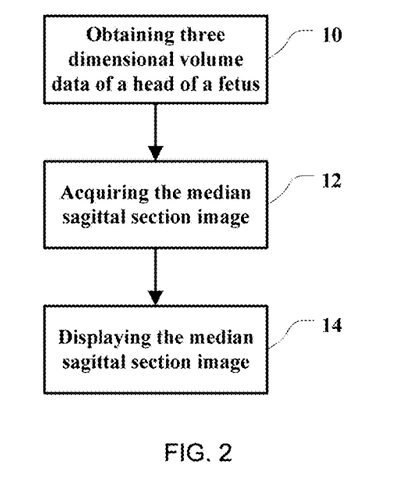
FIG. 2 is a schematic flow chart of a three dimensional ultrasound imaging method according to an embodiment of the present disclosure.

FIG. 2 shows a schematic flow chart of a three dimensional ultrasound imaging method according to an embodiment of the present disclosure.

In this embodiment, in step 10, the three dimensional ultrasound imaging system may scan the head of a fetus, i.e., may transmit ultrasound waves towards the head of the fetus and receive ultrasound echoes, to obtain ultrasound echo signals. The ultrasound echo signals may be processed as described above and thereby three dimensional volume data of the head of the fetus (hereinafter, "three dimensional volume data") may be obtained. The specific processes for scanning the target and processing the ultrasound echo signals to obtain the three dimensional volume data can be the same to or similar with those which are well known in the art and thus will not be described in details herein.

At least one three dimensional volume data of the head of the fetus may be obtained in the step 10.

Figure 3:
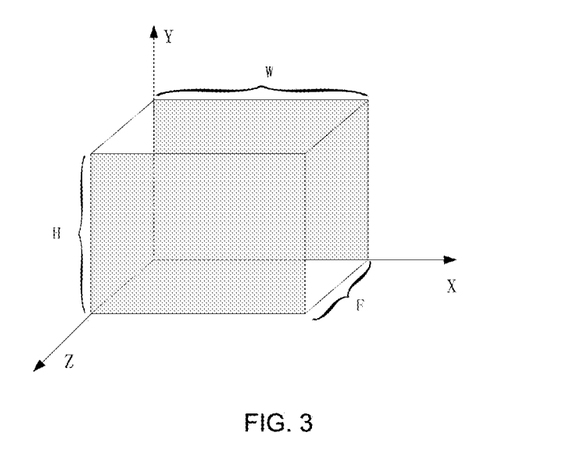
FIG. 3 is a schematic view of a three dimensional volume data according to an embodiment of the present disclosure.

For example, FIG. 3 shows a schematic view of one three dimensional volume data. As shown in FIG. 3, this three dimensional volume data may include F frames of images each of which has size of W×H, where W is the width of the frame and H is the height of the frame. As shown in FIG. 3, the width direction of the frame may be defined as X direction, the height direction of the frame may be defined as Y direction, and the arrangement direction of the frames may be defined as Z direction. However, the X direction, the Y direction and the Z direction may also be defined in other ways.

In the embodiments of the present disclosure, after obtaining the three dimensional volume data in step 10, the median sagittal section image of the head of the fetus may be automatically acquired from the three dimensional volume data.

Figure 4:
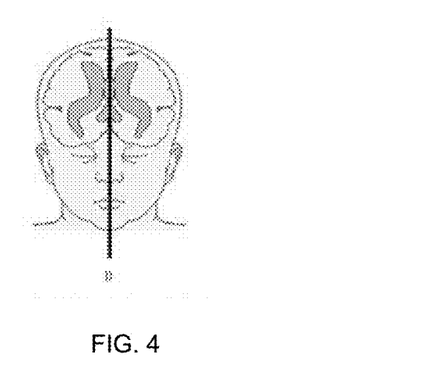
FIG. 4 is a schematic view showing the position of the median sagittal section of a fetal head.
Figure 5:
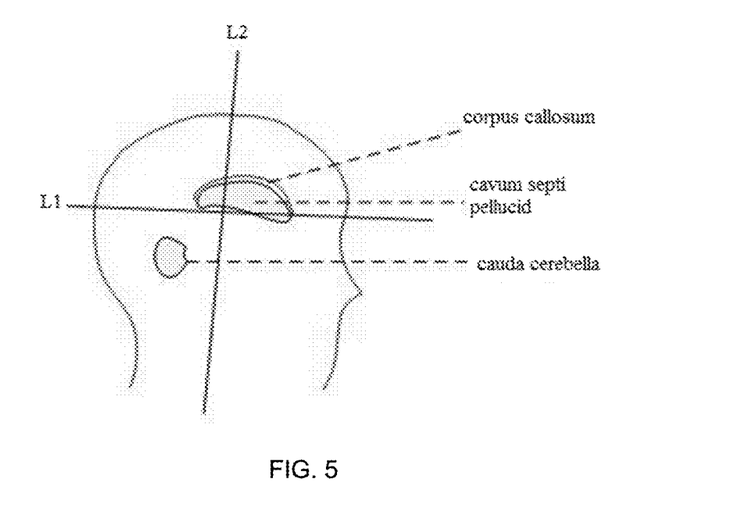
FIG. 5 is a schematic view showing a median sagittal section image of a fetal head.

FIG. 4 schematically shows the position of the median sagittal section in a fetal head, where line D represents the median sagittal section of the fetal head. FIG. 5 shows a schematic view of a median sagittal section image of a fetal head, which shows that the image of the median sagittal section will include important information about the corpus callosum, the cauda cerebella and the cavum septi pellucid (CSP) of the fetus. Furthermore, the cisterna cerebellomedullaris, the interthalamic adhesion and the fourth ventricle, etc. of the fetus may also be observed in the median sagittal section image of a fetal head. Therefore, automatically obtaining and displaying the median sagittal section image of a fetal head can provide important information to the doctors and thus greatly facilitate the observation of the doctors to the fetus.

Figure 6:
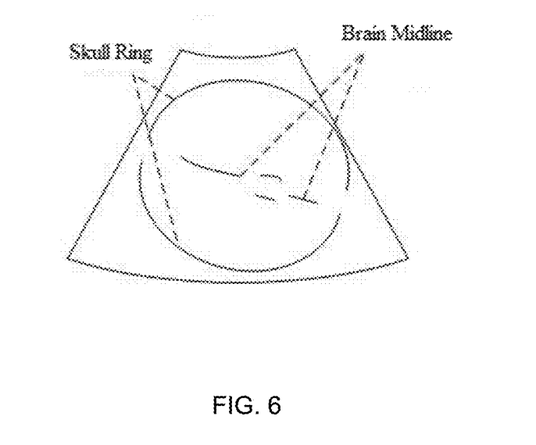
FIG. 6 is a schematic view showing the section image L1 in FIG. 5.
Figure 7:
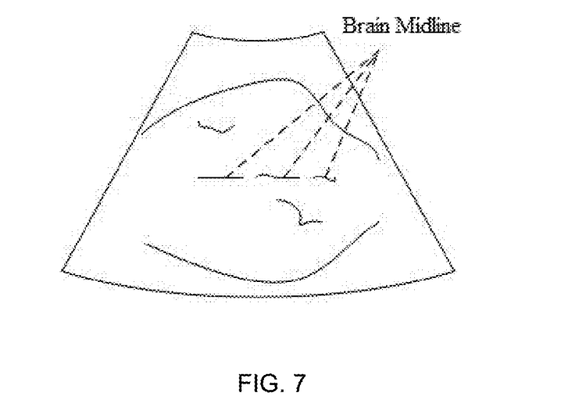
FIG. 7 is a schematic view showing the section image L2 in FIG. 5.

FIG. 6 and FIG. 7 schematically show the schematic views of the section images L1 and L2 which are perpendicular to the median sagittal section image of a fetal head, respectively.

The applicants have found that, among the images of a fetal head, the median sagittal section image has some special characteristics. For example, among all section images of the three dimensional image of a fetal head, the median sagittal section image as a whole has larger gray value than surrounding areas. That is, in the three dimensional image of a fetal head, the median sagittal section image appears as a section image which obviously has larger gray value than the surrounding areas, or, which has larger brightness than the surrounding areas; Or, in a fetal head, the tissue structures outside both sides of the median sagittal section are approximately symmetrical with respect to the median sagittal section. Therefore, the image data of the three dimensional image of a fetal head outside both sides of the median sagittal section image will have approximate symmetry with respect to the median sagittal section image; Or, in a fetal head, the median sagittal section is located at the center position of the fetal head. Therefore, in the three dimensional image of a fetal head, another section image which intersects with the median sagittal section image will contain information at the intersection line of said another section image with the median sagittal section image. In said another section image, the intersection line of said another section image with the median sagittal section image appears as a line with higher brightness, i.e. the brain midline. The collection of the brain midlines form the median sagittal section image; etc. In some embodiments of the present disclosure, these characteristics of the median sagittal section image of a fetal head may be used to detect or identify the median sagittal section image from the three dimensional volume data of a fetal head.

Accordingly, in some embodiments of the present disclosure, in step 12, a median sagittal section image may be acquired from the three dimensional volume data obtained in step 10 using the characteristic(s) of the median sagittal section image of a fetal head (for example, the characteristic(s) mentioned above, for example the gray characteristic).

In the embodiments, entire or a part of the three dimensional volume data of the head of the fetus obtained in step 10 may be used to acquire the median sagittal section image. For example, the part of the three dimensional volume data where the median sagittal section is most likely located may be used to acquire the median sagittal section image, while the part where it is obviously impossible for the median sagittal section to be located may be excluded from the acquisition process. For example, since the median sagittal section of a fetal head is a longitudinal section (i.e., a section in the direction from the top to the neck) located at the center position of a fetal head, it will be impossible for the median sagittal section image to be located in the regions at the edge of the fetal head, which thus can be excluded from the acquisition process.

In the embodiments of the present disclosure, a variety of ways may be used to acquire the median sagittal section image from the three dimensional volume data.

For example, as mentioned above, the median sagittal section image will have larger gray value than surrounding areas in the three dimensional volume data. In some embodiments, this characteristic may be used to acquire the median sagittal section image from the three dimensional volume data.

Figure 8:
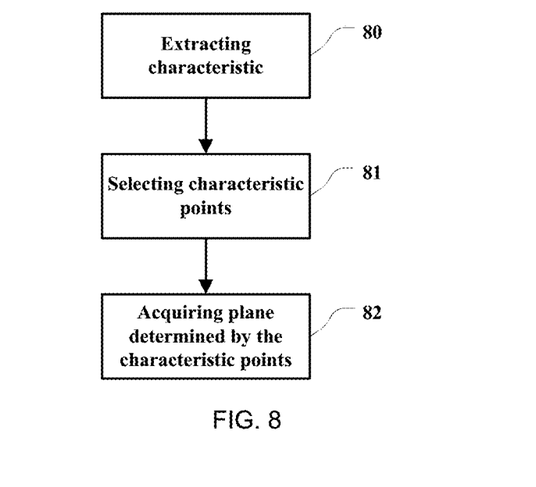
FIG. 8 is a schematic flow chart of the step of acquiring a median sagittal section image according to an embodiment of the present disclosure.

FIG. 8 schematically shows a flow chart of acquiring the median sagittal section image from the three dimensional volume data according to an embodiment of the present disclosure.

In step 80, sagittal section characteristic regions may be extracted from the three dimensional volume data. The sagittal section characteristic regions may represent plane regions which have larger gray values than the areas located outside both sides of the plane regions.

In other words, some characteristic regions may be extracted. The characteristic regions may be plane regions which have larger gray value than the areas located outside both sides of the plane regions. In some embodiments of the present disclosure, these extracted characteristic regions may be the sagittal section characteristic regions mentioned above. This way, the characteristic of "the median sagittal section image having larger gray value than surrounding areas" may be fully utilized to facilitate the acquisition of the median sagittal section image.

In the embodiments of the present disclosure, a variety of suitable ways may be used to extract the sagittal section characteristic regions from the three dimensional volume data. For example, in some embodiments, convolution may be performed on the three dimensional volume data using a characteristic extraction operator to obtain a convolution image, which will contain the sagittal section characteristic regions extracted.

In some embodiments, the convolution may be performed on each frame image of the three dimensional volume data using two-dimensional characteristic extraction operator, respectively, and then the obtained convolution images may be combined to form a three dimensional convolution volume data. In other embodiments, the convolution may also be performed directly on the three dimensional volume data using a three-dimensional characteristic extraction operator designed therefor. The specific steps of the convolution may be well known in the art and thus will not be described in details herein.

In some embodiments, the characteristic extraction operators may be designed according to the image characteristics to be extracted. For example, in the embodiments mentioned above, the sagittal section characteristic regions having larger gray value than the area outside both sides thereof need to be extracted. In this case, one or more of the following characteristic extraction operators may be used:

$$\begin{bmatrix} -1 & -1 & -1 \\ 2 & 2 & 2 \\ -1 & -1 & -1 \end{bmatrix}; \quad (1)$$

$$\begin{bmatrix} -1 & \cdots & -1 \\ & 0 & \\ 2 & \cdots & 2 \\ & 0 & \\ -1 & \cdots & -1 \end{bmatrix}; \quad (2)$$

$$\begin{bmatrix} -1 \\ 0 \\ \cdots \\ 0 \\ 2 \\ 0 \\ \cdots \\ 0 \\ -1 \end{bmatrix}; \quad (3)$$

$$\begin{bmatrix} 1 & 2 & 1 \\ 0 & 0 & 0 \\ -1 & -2 & -1 \end{bmatrix}; \quad (4)$$

$$\begin{bmatrix} -1 & -2 & -1 \\ 0 & 0 & 0 \\ 1 & 2 & 1 \end{bmatrix}. \quad (5)$$

In some embodiments, a characteristic extraction operator obtained by transposition (matrix transposition), rotation or combination of the characteristic extraction operators mentioned above may also be used. In other embodiments, other suitable characteristic extraction operators, such as the Roberts operator, the Laplace Gauss operator or the modification thereof or the like, may also be used.

In some embodiments, a three-dimensional characteristic extraction operator may also be designed.

In some embodiments, the size of the characteristic extraction operator (two-dimensional or three-dimensional) may be set as required.

After the sagittal section characteristic regions are extracted in the step 80, characteristic points which satisfy certain conditions may be selected from the extracted sagittal section characteristic regions in step 81. In general, at least three characteristic points may be selected. The characteristic point parameters of the selected characteristic points may be recorded, which will be used in following steps.

In some embodiments, the "characteristic point parameters" may include the coordinates and/or the value (for example, the gray value or the result value of convolution, etc.) of the characteristic points.

In the embodiments, the "certain conditions" mentioned above may be determined according to the properties of the characteristic extraction operator used. For example, when the characteristic extraction operators (1)-(5) mentioned above are used, the certain conditions may be that the result value of convolution of the point is larger than a certain threshold value. The threshold value may be an empirical parameter and may be determined as required.

In other embodiments, in order to facilitate the following plane detection step (described in details below) and reduce the impact of noise, the points which are obviously not within the head may be excluded according to certain prior knowledge. For example, the head usually is located at the center of the three dimensional volume data. Therefore, the characteristic points may be selected from points which are located within a sphere or ellipsoid centered at the center of the three dimensional volume data and having a radius of a threshold value. This threshold value may also be an empirical parameter or determined as required.

The characteristic points selected in the step 81 usually can determine a plane. According to some embodiments of the present disclosure, this plane may be the plane of the median sagittal section and the section image in the three dimensional volume data which is coincide with this plane may be the median sagittal section image of the head of the fetus. Therefore, in some embodiments, the plane of the median sagittal section of the head of the fetus may be determined by acquiring the plane determined by the selected characteristic points.

The plane determined by a plurality of characteristic points may be acquired by a variety of methods, such as the weighted Hough transformation, the random Hough transformation, the least squares estimation, the Radon transformation, etc.

For example, in an embodiment, the weighted Hough transformation may be used to acquire the plane determined by the selected characteristic points, which will be described in details below.

In a three dimensional space, a plane generally can be expressed as $aX+bY+cZ+d=0$ or $Z=aX+bY+C$ or $Y=aX+bZ+c$, where a, b, c and d are the plane parameters which determine the plane.

Figure 9:
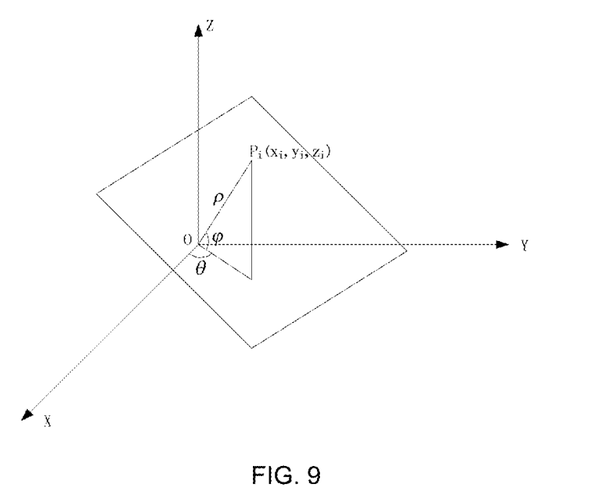
FIG. 9 is a schematic view showing the sections in a three dimensional space and the plane parameters thereof.

In a three dimensional space, the plane may also be expressed as following formula:

$$\rho = \cos\theta \cos\varphi X + \sin\theta \cos\varphi Y + \sin\varphi Z \quad (6),$$

where $\theta$, $\varphi$ and $\rho$ are the plane parameters and their meaning may be those as shown in FIG. 9. One set of $\theta$, $\varphi$ and $\rho$ may determine one plane.

The plane parameters $\theta$, $\varphi$ and $\rho$ in the formula (6) have respective ranges which are related to the way for defining the three dimensional Cartesian coordinate system. For example, for a three dimensional volume data, when the position of the origin of the three dimensional Cartesian coordinate system varies, the ranges of the plane parameters will vary correspondingly.

For example, in the embodiment shown in FIG. 9, the rang of the parameter $\rho$ may be as following:

$$0 \le \rho \le \sqrt{(W-1)^2 + (H-1)^2 + (F-1)^2} \quad (7).$$

W, H and F are the sizes of the three dimensional volume data, where F is the number of the frame images in the three dimensional volume data, W is the width of the frame image and H is the height of the frame image.

It will be understood that when the three dimensional Cartesian coordinate system is defined in other ways, the ranges of the plane parameters $\theta$, $\varphi$ and $\rho$ will be different.

In the three dimensional space corresponding to the three dimensional volume data, there are infinite number of planes which pass through one certain point, i.e., there are infinite number of sets of $\theta$, $\varphi$ and $\rho$, which will form a parameter space (which may be referred to as $\theta$-$\varphi$-$\rho$ space), i.e., a Hough space. The concept of the Hough transformation is projecting the points in the three dimensional space corresponding to the three dimensional volume data into the Hough space and detecting the peak value of the Hough space. The peak value corresponds to the plane in the three dimensional space corresponding to the three dimensional volume data.

Figure 10:
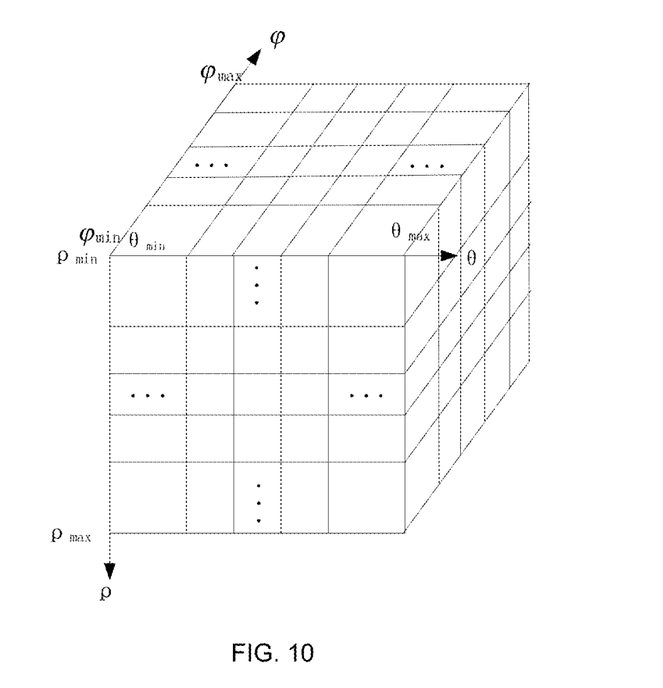
FIG. 10 is a schematic view showing a three dimensional Hough matrix according to an embodiment of the present disclosure.

In some embodiments, $\theta$, $\varphi$ and $\rho$ are continuous. Therefore, $\theta$, $\varphi$ and $\rho$ may be sampled to be divided into a plurality of units (as shown in FIG. 10). Accordingly, the weighted Hough transformation may be performed as following:

S11: calculating ranges and sampling steps of the plane parameters. The range of the parameter $\rho$ may be as shown in formula (7). The largest ranges of the parameter $\theta$ and $\varphi$ may be determined with reference to FIG. 9, such as, $0° \le \theta < 360°$ and $-90° \le \varphi \le 90°$.

In some embodiments, the ranges may also be narrowed according to certain prior knowledge.

The ranges calculated may be expressed as $\theta_{min} \le \theta \le \theta_{max}$, $\varphi_{min} \le \varphi \le \varphi_{max}$ and $\rho_{min} \le \rho \le \rho_{max}$. The sampling steps $\theta_{step}$, $\varphi_{step}$ and $\rho_{step}$ may be determined according to the acquisition accuracy required. For example, in an embodiment, $\theta_{step}=1$, $\varphi_{step}=1$, $\rho_{step}=2$. In other embodiments, the sampling step may also be other value.

S12: generating and initializing the Hough matrix. The Hough matrix may be generated and be initialized to zero. The size of a three dimensional Hough matrix may be:

$$\frac{(\theta_{max}-\theta_{min})}{\theta_{step}} \times \frac{(\varphi_{max}-\varphi_{min})}{\varphi_{step}} \times \frac{(\rho_{max}-\rho_{min})}{\rho_{step}}. \quad (8)$$

In other embodiments, three one-dimensional Hough matrixes may also be used, the sizes of which may be $$\frac{(\theta_{max}-\theta_{min})}{\theta_{step}}, \frac{(\varphi_{max}-\varphi_{min})}{\varphi_{step}} \text{ and } \frac{(\rho_{max}-\rho_{min})}{\rho_{step}},$$

respectively.

S13: Voting the parameters. For example, a voting value $\rho_l$ may be calculated as following for each of the selected characteristic points and each $\theta_j$ and $\varphi_k$ in the range aforementioned:

$$\rho_l = \cos\theta_j \cos\varphi_k X_i + \sin\theta_j \cos\varphi_k Y_i + \sin\varphi_k Z_i \quad (9).$$

Where $(X_i, Y_i, Z_i)$ are the coordinates of the i-th characteristic point Pi.

Then the Hough matrix may be updated as:

$$H(\theta_j,\varphi_k,\rho_l)=H(\theta_j,\varphi_k,\rho_l)+V_i \qquad (10)$$

Where $V_i$ is the value of the i-th characteristic point Pi (for example, the gray value or the result value of convolution, etc.).

S14: detecting peak value of the Hough matrix. The $\theta$, $\varphi$ and $\rho$ corresponding to the peak value of the Hough matrix H may be calculated. Provided that the location of the peak value of the Hough matrix H is $(\theta_j, \varphi_k, \rho_l)$, the plane acquired may be:

$$\theta=\theta_j\theta_{step}+\theta_{min}$$

$$\varphi=\varphi_k\varphi_{step}+\varphi_{min}$$

$$\rho=\rho_l\rho_{step}+\rho_{min} \qquad (11)$$

In the embodiments aforementioned which use three one-dimensional Hough matrixes, the $\theta$, $\varphi$ and $\rho$ corresponding to the peak values of the Hough matrixes may be calculated respectively.

In these embodiments, the weighted Hough transformation takes into account the difference between the contributions of respective characteristic points Pi to the plane acquisition. The larger its value $V_i$, the more it contribute to the Hough matrix.

In some embodiments, the difference between the contributions of respective characteristic points may also not be taken into account. That is, the value $V_i$ of every characteristic point may be set as 1. In this case, the plane determined by these characteristic points may also be acquired. In fact, in this case, the weighted Hough transformation aforementioned is degenerated into a traditional Hough transformation.

In some embodiments, other methods for plane acquisition may also be used. For example, in one embodiment, the plane determined by the selected characteristic points may be acquired by random Hough transformation, the specific steps of which may be as following.

S21: calculating ranges and sampling steps of the plane parameters. In this step, the ranges and the sampling steps of the plane parameters $\theta$, $\varphi$ and $\rho$ may be calculated. This step may be the same as or similar to the step S11 aforementioned.

S22: generating a Hough matrix and initializing it to zero. In this step, a three dimensional Hough matrix may be generated and be initialized to 0. This step may be the same as or similar to the step S12 aforementioned.

S23: selecting points randomly. In this step, three points may be selected randomly from the selected characteristic points.

S24: solving the plane equation to acquire the plane parameters. In this step, the coordinates of the three points may be substituted into the plane equation to solve for the plane parameters $\theta$, $\varphi$ and $\rho$. The specific methods for solving for plane parameters are well known in the art and will not described in details herein.

S25: updating the Hough matrix. In this step, the values at the locations corresponding to the $\theta$, $\varphi$ and $\rho$ in the Hough matrix may be increased by 1.

S26: repeating the steps S23 to S25 for N times. N herein may be a predefined parameter, and may be set as required. For example, in an embodiment, N may be 50000. In other embodiments, N may be other value.

S27: detecting the peak value of the Hough matrix. In this step, the location in the Hough matrix which has maximum value may be acquired and the $\theta$, $\varphi$ and $\rho$ corresponding to the location represent the plane acquired.

In some embodiments of the present disclosure, the steps of another method (which is referred to as stochastic optimal energy method herein) for acquiring the plane determined by the selected characteristic points may be as following.

S31: initializing an optimal energy E_best=0.

S32: selecting points randomly. In this step, three points may be selected randomly from the selected characteristic points.

S33: solving equations. In this step, the coordinates of the three points may be substituted into plane equations to solve for the plane parameters $\theta$, $\varphi$ and $\rho$.

S34: calculating current energy E. In this step, an "energy" E of the selected characteristic points from which the distances to the plane acquired in step S33 are less than $\varepsilon$ may be calculated.

In this step, the distance from each characteristic point Pi of the selected characteristic points to the plane $(\theta,\varphi,\rho)$ acquired in step S33 may be calculated. When the distance is less than $\varepsilon$, the value $V_i$ of the current characteristic point may be accumulated to the energy E, i.e., E=E+$V_i$. $\varepsilon$ is a parameter which may be set as required. For example, in an embodiment, $\varepsilon$ may be set as 5. $\varepsilon$ may also be set as other value.

S35: updating the energy. If the current energy E>E_best, E_best may be set as E and the current plane parameters may be updated as the optimal plane parameters. Otherwise, it turns to step S36.

S36: repeating steps S32 to S35 for N times. N is iteration times and may be set as required.

S37: outputting the plane parameters. After the step S36 is completed, the plane parameters corresponding to the iteration with maximum energy may be outputted as acquired plane parameters.

In this way, one plane determined by the select characteristic points may be acquired.

In some embodiments, in the step S34, the value $V_i$ of the current characteristic point may also not be accumulated. Rather, when the distance from point Pi to the plane is less than $\varepsilon$, E=E+1. That is, the contributions of the selected characteristic points to the plane acquisition are considered as to be the same.

In the embodiments above, the plane expression in formula (6) is used. The plane is acquired by calculating the coefficients $\theta$, $\varphi$ and $\rho$ of the formula. However, the form of the plane expression does not affect the methods of the embodiments. The methods described above are also suitable for other plane expression such as aX+bY+cZ+d=0, Z=aX+bY+c or Y=aX+bZ+c after simple modification.

As described above and with further reference to FIG. 4 to FIG. 7, in the three dimensional image of the head of the fetus, the median sagittal section is the longitudinal section located at the middle of the head of the fetus, and other section images which intersect with the median sagittal section image will contain information at the intersection position of said other section images with the median sagittal section image, in other words, will contain information at the intersection line. In said other section image, the intersection line of said other section image with the median sagittal section image appear as a line with higher brightness (because, as described above, in the three dimensional image or the three dimensional volume data of a fetal head, the median sagittal section image has larger brightness than surrounding areas), i.e., the brain midline. The collection of the brain midlines forms the median sagittal section image. Therefore, in some embodiments of the present disclosure, these characteristics may be used to acquire the median sagittal section image from the three dimensional volume data.

Figure 11:
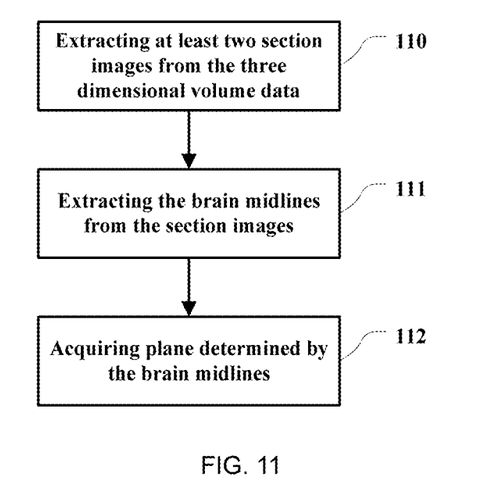
FIG. 11 is a schematic flow chart of the step of acquiring a median sagittal section image according to another embodiment of the present disclosure.

For example, in some embodiments, a schematic flow chart of acquiring the median sagittal section image from the three dimensional volume data may be as shown in FIG. 11.

In some embodiments, in step 110, at least two section images may be extracted from the three dimensional volume data. The section images may be extracted in different ways. For example, the section images which are parallel to the section L2 in FIG. 5 and/or parallel to the section L1 in FIG. 5 may be extracted. Or, any other suitable section images may be extracted, such as the section images which are at certain angles with respect to the section L2 and/or the section L1. The number of the extracted section images may also not be limited.

After the section images are extracted, in step 111, the brain midline may be extracted from each of the section images to thereby obtain a plurality of straight lines representing the brain midline.

A brain midline appears as a straight line in a section image which has larger gray value than the areas outside both sides thereof. Therefore, the extraction of the brain midline may be realized based on this characteristic.

In some embodiments, extracting the brain midline from each of the extracted section image may include following steps.

S40: extracting brain midline characteristic regions.

In some embodiments, the brain midline characteristic regions which are in accordance with the characteristic of the brain midline aforementioned, i.e., the brain midline characteristic regions which represent lines having larger gray value than areas outside both sides thereof, may be extracted from said section image. The methods for extracting the brain midline characteristic regions may be similar to the methods for extracting the sagittal section characteristic regions aforementioned. For example, convolution may be performed on said section image using characteristic extraction operators. The section image processed by the convolution contains the extracted brain midline characteristic regions.

It should be understood that the "line" and the "brain midline" mentioned herein should not be ideally interpreted as theoretical lines, but regions having certain width and/or thickness.

The characteristic extraction operator may be designed based on the characteristics of the brain midline to be extracted. In some embodiments, the characteristics of the brain midline are similar to the characteristics of the median sagittal section described above. Therefore, the characteristic extraction operator which is similar to the characteristic extraction operator described above, such as similar to any one of the operators (1) to (5), may be used.

After the brain midline characteristic regions are extracted, at least two characteristic points which satisfy certain conditions may be selected from the brain midline characteristic regions, and characteristic point parameters of the at least two characteristic points may be recorded. The characteristic point parameters of the characteristic point may include the coordinates of the characteristic point and/or the value of the characteristic point (for example, the gray value or the result value of convolution) or other suitable parameters.

The certain conditions mentioned herein may be determined based on the properties of the characteristic extraction operator used. For example, when the operators similar to the characteristic extraction operators (1) to (5) above are used, the certain condition may be set as that the result value of convolution of the point is greater than a threshold. The threshold may be an empirical parameter and may be determined as required.

S41: acquiring straight lines.

The selected characteristic points usually determine straight lines. In some embodiment of the present disclosure, the straight line determined by the selected characteristic points may be acquired, which represents the brain midline in the section image.

The weight Hough transformation, the random Hough transformation and the stochastic optimal energy method described above may also be suitable for acquiring the straight lines in the present step after simple modification in details.

For example, the standard equation of a straight line may be $\rho = \cos\theta X + \sin\theta Y$, which has two parameters $\theta$ and $\rho$. Compared to the plane equation, there is no the parameter cp. When the weighted Hough transformation or the random Hough transformation is used, the Hough matrix is a two dimensional $\rho\_\theta$ matrix. When the random Hough transformation or the stochastic optimal energy method is used, two points may be randomly selected from the selected characteristic points for each iteration, which may be enough to acquire a straight line. The other parts of the methods for acquiring the straight line may be substantially similar to the methods for acquiring the plane described above and will not be described in details herein.

In some embodiments, other methods may also be used to acquire the straight line determined by the selected characteristic points, for example, including, but not limited to, randon transformation, phase encoding or least square estimation, etc.

Based on the characteristics of the median sagittal section image in the three dimensional image of a fetal head, the brain midline straight lines acquired will determine a plane. This plane determined by the brain midline straight lines may be the plane on which the median sagittal section image is located.

Therefore, after the brain midline straight lines in the extracted section images are acquired in the step 111, the plane determined by the brain midline straight lines may be acquired in step 112. In this way, the plane on which the median sagittal section is located, i.e., the plane on which the median sagittal section image of the head of the fetus is located, may be acquired.

A variety of methods may be used to acquire the plane determined by the brain midline straight lines. For example, in some embodiments, three points which are not collinear may be selected from the acquired brain midline straight lines. The coordinates of the three points may be substituted into the plane equation to calculate the plane parameters. In other embodiments, these steps may be performed for several times and the average of the results of the acquisition will be the final acquisition result.

Another method may also be used. N points may be selected from the acquired brain midline straight lines and the plane parameters may be fitted using least square estimation. In other embodiments, the N points selected may serve as inputs and the plane parameters may be acquired using the Hough transformation, the random Hough transformation, the stochastic optimal energy method or the like which are similar to those described above.

As described above and with further reference to FIG. 4, the tissue structures outside both sides of the median sagittal section in a fetal head are approximate symmetrical with respect to the median sagittal section, therefore the image data of the three dimensional image of a fetal head outside both sides of the median sagittal section image will have approximate symmetry with respect to the median sagittal section image. In some embodiments, this characteristic may be used to acquire the median sagittal section image from the three dimensional volume data. For example, a plurality of candidate section images may be selected from the three dimensional volume data and the symmetry of the areas outside both sides of the candidate section images may be calculated. The candidate section image with best symmetry of areas outside both sides thereof may be the median sagittal section image desired.

Figure 12:
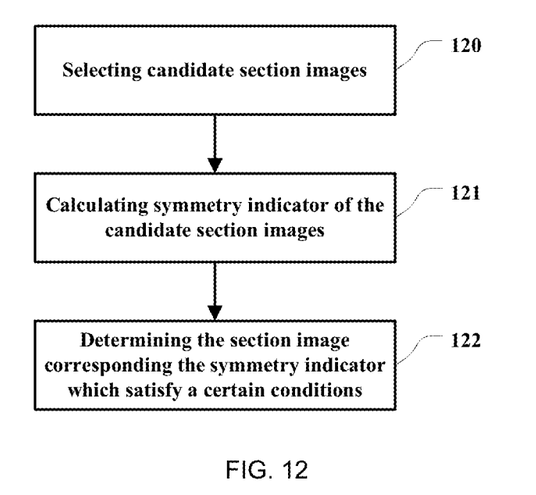
FIG. 12 is a schematic flow chart of the step of acquiring a the median sagittal section image according to still another embodiment of the present disclosure.

For example, in some embodiments, a schematic flow chart of acquiring the median sagittal section image from the three dimensional volume data may be as shown in FIG. 12.

In step 120, a group of candidate section images may be selected from the three dimensional volume data. The candidate section images may be selected as required. For example, in some embodiments, the candidate section images may be all section images which are a certain spacing (or step) apart from each other in one or more certain directions within a certain range in the three dimensional volume data. Herein, the "certain range" may be a angle range with respect to one or more lines and/or planes in the three dimensional volume data, or, may also be a distance range with respect to one or more points, lines and/or planes in the three dimensional volume data; the "in one or more certain directions" may mean that the normal line of the section image is in said one or more certain directions; the "spacing" or "step" may be a distance spacing or step, or a angle spacing or step.

In some embodiments, all section images which are certain spacing or step apart from each other in one or more certain directions within whole of the three dimensional volume data may be selected. In other embodiments, some prior knowledge may be used to assist the selection of the candidate section images to exclude the section images for which it is impossible to be the median sagittal section image. For example, since the median sagittal section of the head of the fetus is a longitudinal section (i.e., a section in the direction from the top to the neck of the fetus) which is located at the center position of the head of the fetus, the longitudinal section images which are located substantially at the center position of the head may be selected as the candidate section images based on the direction of the fetus image in the three dimensional volume data. In the present disclosure, the section images in the direction from the top portion to the neck portion of the fetus in all, or at least a part, of the three dimensional volume data (in other words, the section images which are substantially parallel to the direction from the top portion to the neck portion of the fetus, or the section images whose normal lines are substantially perpendicular to the direction from the top portion to the neck portion of the fetus) may be referred to as "longitudinal section image" of the three dimensional volume data.

Therefore, in some embodiments, a group of longitudinal section images in the three dimensional volume data may be selected as the candidate section images. For example, a group of longitudinal section images which are located at the center position of the head of the fetus (for example, all longitudinal section images which are a certain spacing or step apart from each other within a certain region at the center of the head) may be selected as the candidate section images.

In other embodiments, user inputs which indicate the possible range of the median sagittal section image may be received. Then, the section images within the range indicated by the user may be selected as the candidate section images.

In some embodiments, all section images which are a certain step apart from each other in whole of the three dimensional volume data may be selected as the candidate section images. That is, all section images within the whole three dimensional volume data may be searched using a certain step.

For example, in some embodiments, when the plane equation in the formula (6) is used, the candidate section images may be selected by determining the ranges of the plane parameters $\theta$, $\varphi$ and $\rho$ and the values of the steps $\theta_{step}$, $\varphi_{step}$ and $\rho_{step}$.

Similarly, when the plane equation aX+bY+cZ+d=0, Z=aX+bY+c or Y=aX+bZ+c is used, the candidate section images may be selected by determining the ranges of a, b, c and d and their steps.

For example, when all section images which are a certain step apart from each other in the whole of the three dimensional volume data are selected as the candidate section images, the rang of $\rho$ may be as shown in the formula (7) and the largest ranges of $\theta$ and $\varphi$ may be, for example, $0°\leq\theta<360°$ and $-90°\leq\varphi\leq90°$ (with reference to FIG. 9). It will be understood that when the coordinate system is defined in different way the ranges of the parameters will be different.

The steps $\theta_{step}$, $\varphi_{step}$ and $\rho_{step}$ may be determined based on the acquisition accuracy required and are not limited by the present disclosure. For example, in an embodiments, $\theta_{step}=1$, $\varphi_{step}=1$, $\rho_{step}=2$. It will be understood that the steps may also be other values based on the acquisition accuracy required.

After the candidate section images are selected, a symmetry indicator may be calculated for each candidate section image $(\rho,\theta,\varphi)$.

The symmetry indicator may be used to measure the similarity of the data located outside both sides of the candidate section image.

For example, in some embodiments, for each candidate section image, at least one pair of first region and second region, which are located outside both sides of the candidate section image in the three dimensional volume data, may be selected. The first region and the second region are symmetrical with respect to the candidate section image. Then the data in the first region and the data in the second region may be used to calculate the symmetry indicator of the candidate section image.

Herein, the "data in the first region" may refer to the values of the data points of the three dimensional volume data which are located in the first region. Similarly, the "data in the second region" may refer to the values of the data points of the three dimensional volume data which are located in the second region.

In some embodiments, for each candidate section image, a plurality of pairs of first region and second region may be selected. A symmetry indicator may be calculated for each pair of first region and second region. Therefore a plurality of symmetry indicators may be obtained. Then, the symmetry indicator of the candidate section image may be obtained based on the plurality of symmetry indicators. For example, the symmetry indicator of the candidate section image may be the average of the plurality of symmetry indicators; or the symmetry indicator of the candidate section image may be the weighted average of the plurality of symmetry indicators, where the weighted coefficients may be determined based on the location of the selected pair of first region and second region and other factors; etc. In some embodiments, the final symmetry indicator of the candidate section image may be a function of the plurality of symmetry indicators.

The symmetry indicator may be calculated by a variety of ways.

For example, in some embodiments, the symmetry indicator may be the sum of the absolute value of the difference between the gray values of the corresponding points in the first region and in the second region. I.e., $$E = \sum_{I_L, I_R \in \Omega} |I_L - I_R| \tag{12}$$

Where E is the symmetry indicator, S2 is the first region and the second region, $I_L$ is the data value of the point in the first region, and $I_R$ is the data value of the point in the second region which is symmetrical with the point in the first region with respect to the candidate section image. The "corresponding points in the first region and in the second region" mentioned above may refer to the points in the first region and in the second region which are symmetrical with respect to the candidate section image.

In some embodiments, the symmetry indicator of the candidate section image may also be the correlation coefficient between the first region and the second region. I.e., $$E = \frac{\sum_{I_L, I_R \in \Omega} I_L I_R}{\sqrt{\sum_{I_L \in \Omega} I_L^2} \sqrt{\sum_{I_R \in \Omega} I_R^2}} \tag{13}$$

Where E is the symmetry indicator, $\Omega$ is the first region and the second region, $I_L$ is the data value of the point in the first region, and $I_R$ is the data value of the point in the second region which is symmetrical with the point in the first region with respect to the candidate section image.

The symmetry indicator may be defined as described above, but not limited to. Other definitions may also be used. For example, the symmetry indicator may also be the Euclidean distance between the first region and the second region, the cosine similarity between the first region and the second region, or the like.

The symmetry indicators may be calculated for all candidate section images and thus a group of symmetry indicators may be obtained. Then, a characteristic symmetry indicator which satisfies characteristic conditions may be selected from the group of symmetry indicators. According to some embodiments, the candidate section image corresponding to the characteristic symmetry indicator is the median sagittal section image of the head of the fetus desired.

The "characteristic conditions" herein may be conditions which indicate the optimal symmetry of the candidate section image. The characteristic conditions may be determined based on the ways for calculating the symmetry indicators. For example, for the symmetry indicator calculated using the formula (12), the smaller the E (i.e. the symmetry indicator), the more similar the image pixels outside both sides of the candidate section image, i.e., the better the symmetry. Therefore, in this case, the characteristic condition may be that "the symmetry indicator is the smallest".

While for the symmetry indicator calculated using the formula (13), the larger the E (i.e., the similarity indicator) (for the formula (13), the closer to 1 the E), the more similar the image pixels outside both sides of the candidate section image, i.e., the better the symmetry. Therefore, in this case, the characteristic condition may be that "the symmetry indicator is the closest to 1" or "the symmetry indicator is the largest".

When the symmetry indicators are calculated in other ways, the characteristic conditions may be accordingly defined. For example, when the symmetry indicator is the Euclidean distance between the first region and the second region, the characteristic condition may be that "the symmetry indicator is the smallest". That is, in this case, the smaller the symmetry indicator (i.e., the smaller the Euclidean distance), the better the symmetry of the first region with the second region. When the symmetry indicator is the cosine similarity between the first region and the second region, the characteristic condition may be that "the symmetry indicator is the largest". That is, the larger the symmetry indicator (i.e., the larger the cosine similarity), the better the symmetry of the first region with the second region.

As described above, some special structures will be shown in the median sagittal section image of a fetal head. In other words, the median sagittal section image of a fetal head will contain some special structural features. In some embodiments, this characteristic of the median sagittal section image of a fetal head may be used. A template image (or standard reference image) of the median sagittal section image of a fetal head may be generated using the median sagittal section images of fetal heads which have been obtained previously. Then, in the three dimensional imaging process, the section images of the obtained three dimensional volume data may be matched with the template image and the similarity between the section images of the three dimensional volume data and the template image may be calculated. The section image in the three dimensional volume data with largest similarity with the template image may be the median sagittal section image of the head of the fetus.

Figure 13:
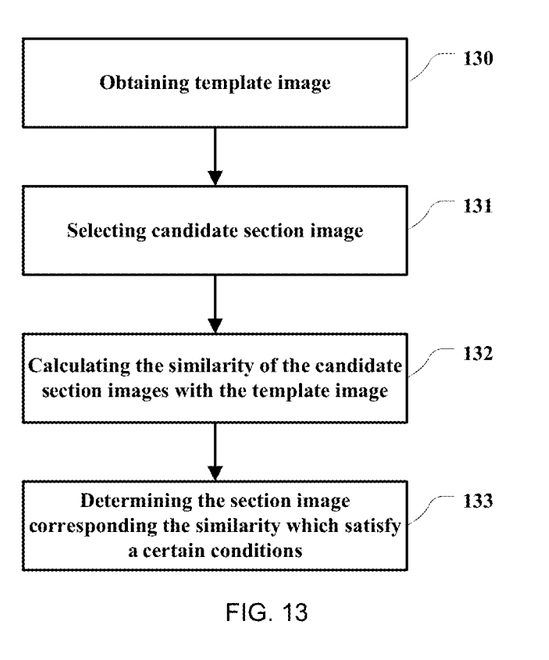
FIG. 13 is a schematic flow chart of the step of acquiring a the median sagittal section image according to still another embodiment of the present disclosure.

For example, in some embodiments, a schematic flow chart of acquiring the median sagittal section image from the three dimensional volume data may be as shown in FIG. 13.

In step 130, a template image of the median sagittal section image of a fetal head may be obtained. In some embodiments, the template image may be generated based on the median sagittal section images of the head of other fetuses which have been obtained previously and be stored in a memory. In the three dimensional imaging process, the template image may be read from the memory. In other embodiments, the template image may also be generated in the three dimensional imaging process.

The template image may be one or more. For example, a plurality of template images may be used to match the section images of three dimensional volume data with different size.

When a plurality of template images are used, each candidate section image may be matched with each template image.

After the template images are obtained, a group of candidate section images may be selected from the three dimensional volume data in step 131. The candidate section images may be selected as required. For example, in some embodiments, the candidate section images may be all section images which are a certain spacing (or step) apart from each other in one or more certain directions within a certain range in the three dimensional volume data. Herein, the "certain range" may be a angle range with respect to one or more lines and/or planes in the three dimensional volume data, or, may also be a distance range with respect to one or more points, lines and/or planes in the three dimensional volume data; the "in one or more certain directions" may mean that the normal line of the section image is in said one or more certain directions; the "spacing" or "step" may be a distance spacing or step, or a angle spacing or step.

In some embodiments, all section images which are certain spacing or step apart from each other in one or more certain directions within whole of the three dimensional volume data may be selected. In other embodiments, some prior knowledge may be used to assist the selection of the candidate section images to exclude the section images for which it is impossible to be the median sagittal section image. For example, since the median sagittal section of a fetal head is a longitudinal section (i.e., a section in the direction from the top to the neck of the fetus) which is located at the center position of the fetal head, the longitudinal section images which are located substantially at the center position of the head may be selected as the candidate section images based on the direction of the fetus image in the three dimensional volume data. For example, a group of longitudinal section images which are located at the center position of the head of the fetus (for example, all longitudinal section images which are a certain spacing or step apart from each other within a certain region at the center of the head) may be selected as the candidate section images.

In other embodiments, user inputs which indicate the possible range of the median sagittal section image may be received. Then, the section images within the range indicated by the user may be selected as the candidate section images.

In some embodiments, all section images which are a certain step apart from each other in whole of the three dimensional volume data may be selected as the candidate section images. That is, all section images within the whole three dimensional volume data may be matched with the template image with a certain step.

For example, in some embodiments, when the plane equation in the formula (6) is used, the candidate section images may be selected by determining the ranges of the plane parameters θ, φ and ρ and the values of the steps $\theta_{step}$, $\varphi_{step}$ and $\rho_{step}$.

Similarly, when the plane equation aX+bY+cZ+d=0, Z=aX+bY+c or Y=aX+bZ+c is used, the candidate section images may be selected by determining the ranges of a, b, c and d and their steps.

For example, when all section images which are a certain step apart from each other in the whole of the three dimensional volume data are selected as the candidate section images, the rang of ρ may be as shown in the formula (7) and the largest ranges of θ and φ may be, for example, 0°≤θ≤360° and −90°≤φ≤90° (with reference to FIG. 9). It will be understood that when the coordinate system is defined in different way the ranges of the parameters will be different.

The steps $\theta_{step}$, $\varphi_{step}$ and $\rho_{step}$ may be determined based on the acquisition accuracy required and are not limited by the present disclosure. For example, in an embodiments, $\theta_{step}=1$, $\varphi_{step}=1$, $\rho_{step}=2$. It will be understood that the steps may also be other values based on the acquisition accuracy required.

As described above, in some embodiments, only one template image is used. In this case, the template image may be generated in a certain size. Before the candidate section images are selected from the three dimensional volume data, the methods may further include a step of aligning the three dimensional volume data and the template image. In this step, the three dimensional volume data and the template image may be aligned to a same scale space. In other words, the sizes of the corresponding structures in the three dimensional volume data and in the template image are made to be approximately the same. By this alignment, the corresponding structures in the three dimensional volume data and in the template image have approximately same sizes. Thereby the match is easier to be realized, the match effect is better and the calculation of the match is reduced.

When aligning the three dimensional volume data and the template image, special structural features (for example, the skull ring, etc.) in a section image (for example, the most middle frame of image, i.e., the F/2-th frame of image, or the frame of image near the most middle frame or other frame of image, or other section image) in the three dimensional volume data may be detected, and then the three dimensional volume data may be converted into the same scale with the template image by rotation, translation and/or zooming based on the size of the detected structural features.

Herein, converting the three dimensional volume data into the same scale with the template image may refer to making the same or corresponding structural features in the three dimensional volume data and in the template image to have same size by conversion.

Herein, the "same" may refer to that they are substantially the same or similar, but not be strictly limited to be exactly the same. Rather, there may be a certain difference. In other words, the "same" herein should not be strictly ideally interpreted.

In some embodiments, any other suitable method may also be used to aligning the three dimensional volume data and the template image to the same scale space.

Herein, the "same" may also refer to that they are substantially the same or similar, but not be strictly limited to be exactly the same. Rather, there may be a certain difference. In other words, the "same" herein should also not be strictly ideally interpreted.

After the candidate section images are selected, each of the candidate section images may be matched with the template image in step 132. For example, a similarity indicator of each candidate section image with the template image may be calculated.

The similarity indicator may be used to measure the similarity of the candidate section image with the template image. In the embodiments of the present disclosure, the similarity indicator may be calculated using a variety of ways.

For example, in some embodiments, the similarity indicator may be the sum of the absolute value of the difference between the gray values of the corresponding points in the candidate section image and in the template image. I.e., $$E = \sum_{I_L, I_R \in \Omega} |I_L - I_R| \tag{14}$$

Where E is the similarity indicator, Ω is image space of the candidate section image, $I_L$ is the data value of the point in the candidate section image, and $I_R$ is the data value of the point in the template image corresponding to the point in the candidate section image. Herein, the "corresponding points in the candidate section image and in the template image"

mentioned above may refer to the points in the candidate section image and in the template image which have same location.

In some embodiments, the similarity indicator may also be the correlation coefficient between the candidate section image and the template image. I.e., $$E = \frac{\sum_{I_L, I_R \in \Omega} I_L I_R}{\sqrt{\sum_{I_L \in \Omega} I_L^2} \sqrt{\sum_{I_R \in \Omega} I_R^2}} \quad (15)$$

Where E is the similarity indicator, S2 is the image space of the candidate section image, $I_L$ is the data value of the point in the candidate section image, and $I_R$ is the data value of the point in the template image corresponding to the point in the candidate section image.

The similarity indicator may be defined as described above, but not limited to. Other definition may also be used.

The similarity indicators of all candidate section images may be calculated and thus a group of similarity indicators may be obtained. Then, a characteristic similarity indicator which satisfies characteristic conditions may be selected from the group of similarity indicators. According to some embodiments, the candidate section image corresponding to the characteristic similarity indicator is the desired median sagittal section image of the head of the fetus.

The "characteristic conditions" herein may be conditions which indicate the optimal similarity of the candidate section image with the template image. The characteristic conditions may be determined based on the ways for calculating the similarity indicators.

For example, for the similarity indicator calculated using the formula (14), the smaller the E (i.e. the similarity indicator), the more similar the candidate section image with the template image, i.e., the better the similarity. Therefore, in this case, the characteristic condition may be that "the similarity indicator is the smallest".

While for the similarity indicator calculated using the formula (15), the larger the E (i.e., the similarity indicator) (for the formula (15), the closer to 1 the E), the more similar the candidate section image with the template image, i.e., the better the similarity. Therefore, in this case, the characteristic condition may be that "the similarity indicator is the closest to 1" or "the similarity indicator is the largest".

When the similarity indicators are calculated in other ways, the characteristic conditions may be accordingly defined. For example, when the similarity indicator is the Euclidean distance between the candidate section image and the template image, the characteristic condition may be that "the similarity indicator is the smallest". That is, in this case, the smaller the similarity indicator (i.e., the smaller the Euclidean distance), the better the similarity of the candidate section image with the template image. When the similarity indicator is the cosine similarity between the candidate section image and the template image, the characteristic condition may be that "the similarity indicator is the largest". That is, the larger the similarity indicator (i.e., the larger the cosine similarity), the better the similarity of the candidate section image with the template image.

In the embodiments of the present disclosure, after being acquired in the steps described above, the median sagittal section image of the head of the fetus may be displayed on the display for the observation of the doctors.

In some embodiments of the present disclosure, the automatic acquisition of the sagittal section image may essentially be indicating the location of the sagittal section image in the three dimensional volume data. However, the expression of the result of the acquisition may vary, such as the plane equation, the translation (in X, Y and Z directions) and rotation (about the X axis, Y axis and Z axis) of the sagittal section image with respect to the origin of the coordinate system, the transformation matrix of the sagittal section image with respect to the original coordinate system (in general one 4×4 matrix can represent the transformation relation between two coordinate systems), and even the spatial coordinates of three points (since three points can determine a plane), etc. These expressions may essentially be indication of the location of a plane in the coordinate system of a three dimensional volume data. These expressions can be converted to each other.

In the embodiments described above, the expression of plane equation is used for the convenience of description. However, the present disclosure is not limited to the expression of plane equation. Rather, other expressions described above or in the art may also be used. The expressions of the result of the acquisition of the sagittal section image only differ in expression form, which does not affect the essence of the present disclosure, and therefore are all in the scope of protection of the present disclosure.

The three dimensional ultrasound imaging methods according to the embodiments described above may be implemented by the three dimensional ultrasound imaging system described with reference to FIG. 1. The three dimensional ultrasound imaging system may include the probe 2, the three dimensional imaging unit 8 and the display 9. The probe 2 may transmit ultrasound waves towards the head of the fetus and receive the ultrasound echoes to obtain the ultrasound echo signals. The three dimensional imaging unit 8 may obtain the three dimensional volume data of the head of the fetus based on the ultrasound echo signals and acquire the median sagittal section image of the head of the fetus using the method according to any one of the embodiments described above. The acquired median sagittal section image may be displayed on the display 9.

In the embodiments of the present disclosure, the three dimensional ultrasound imaging system may further include other components, such as the transmitting/receiving switch 3, the transmitting circuit 4, the receiving circuit 5, the beamformer unit 6 and the signal processing unit 7, etc. as shown in FIG. 1, which will not be described in details herein.

In the embodiments of the present disclosure, the three dimensional ultrasound imaging systems which implement the methods according to the embodiments described above are not limited to the ultrasound imaging systems which are integrated as a single device (for example, the cart-type ultrasound imaging system or portable ultrasound imaging system), but may also be distributed systems. For example, at least a part of the steps or functions of the methods according to the embodiments described above may be implemented in other devices (for example, data processing work stations, personal computers, smart portable devices, another ultrasound imaging device, network servers, or the like) which are connected to general cart-type ultrasound imaging system or portable ultrasound imaging system by data communication devices (wired or wireless) to thereby together form the three dimensional ultrasound imaging system according to some embodiments of the present disclosure.

In the ultrasound imaging methods according to the present disclosure, the fetus may be scanned by ultrasound waves and the three dimensional volume data of the head of the fetus may be obtained. The median sagittal section image of the head of the fetus may be automatically obtained and displayed. The problem that it is difficult for the doctors to precisely position the median sagittal section image may be solved. Therefore, the doctor can conveniently observe the median sagittal section image of the head of the fetus and a large amount of important information may be presented to the doctor.

Although the present disclosure has been described through specific embodiments, the present disclosure is not limited to the specific embodiments described above. Those of skill in the art should understand that various modifications, alternatives and variations may be made based on the present disclosure, which all should be within the scope of protection of the present disclosure. Furthermore, "a (an) embodiment" or "another embodiment" mentioned above may represent different embodiments, or may also be combined completely or partly in one embodiment.

What is claimed is:

1. A three-dimensional ultrasound imaging method, comprising:

transmitting ultrasound waves towards a head of a fetus;

receiving ultrasound echoes to obtain ultrasound echo signals;

obtaining a three-dimensional volume data of the head of the fetus based on the ultrasound echo signals;

obtaining template image of a median sagittal section image of a fetal head generated based on median sagittal section images of fetuses which have been obtained previously;

selecting a group of candidate section images from the three-dimensional volume data;

calculating a similarity indicator for each candidate section image of the group of candidate section images with the template image to obtain a group of similarity indicators;

selecting a similarity indicator which satisfies a characteristic condition from the group of similarity indicators;

using the selected similarity indicator to identify the corresponding candidate selection image as a median sagittal section image of the head of the fetus; and displaying the median sagittal section image.

2. The method of claim 1, wherein the group of candidate section images is a group of longitudinal section images of the three-dimensional volume data.

3. The method of claim 1, wherein, before selecting a group of candidate section images from the three-dimensional volume data, the method comprises aligning the three-dimensional volume data and the template image to a same scale space.

4. The method of claim 3, wherein aligning the three-dimensional volume data and the template image to a same scale space comprises: detecting special structural features in section images of the three-dimensional volume data; and converting the three-dimensional volume data into a same scale with the template image based on sizes of the special structural features.

5. The method of claim 1, wherein the similarity indicator comprises a sum of absolute values of differences between gray values of corresponding points in the candidate section image and in the template image, wherein the characteristic condition is that the similarity indicator is the smallest.

6. The method of claim 1, wherein the similarity indicator comprises a correlation coefficient between the candidate section image and the template image, wherein the characteristic condition is that the similarity indicator is the largest.

7. The method of claim 1, wherein the similarity indicator comprises a Euclidean distance between the candidate section image and the template image, wherein the characteristic condition is that the similarity indicator is the smallest.

8. The method of claim 1, wherein the similarity indicator comprises a cosine similarity between the candidate section image and the template image, wherein the characteristic condition is that the similarity indicator is the largest.

9. A three-dimensional ultrasound imaging method, comprising:

transmitting ultrasound waves towards a head of a fetus;

receiving ultrasound echoes to obtain ultrasound echo signals;

obtaining three-dimensional volume data of the head of the fetus based on the ultrasound echo signals;

extracting at least two section images from the three-dimensional volume data;

extracting brain midlines from the at least two section images to obtain at least two brain midlines, wherein the brain midlines have larger gray values than areas located outside both sides of the brain midlines;

determining a plane on which a median sagittal section image is located based on a plane determined by the at least two brain midlines;

and displaying the median sagittal section image.

* * * * *